(12) United States Patent
Schleyer et al.

(10) Patent No.: US 12,033,729 B2
(45) Date of Patent: Jul. 9, 2024

(54) SYSTEMS AND METHODS FOR ACCESSING, COMBINING AND COLLABORATIVE FILTERING OF INFORMATION FROM MULTIPLE ELECTRONIC HEALTH RECORDS

(71) Applicant: Indiana University Research and Technology Corporation, Indianapolis, IN (US)

(72) Inventors: Titus Karl Ludwig Schleyer, Indianapolis, IN (US); Xia Ning, Columbus, OH (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 441 days.

(21) Appl. No.: 16/330,674

(22) PCT Filed: Sep. 6, 2017

(86) PCT No.: PCT/US2017/050306
§ 371 (c)(1),
(2) Date: Mar. 5, 2019

(87) PCT Pub. No.: WO2018/048921
PCT Pub. Date: Mar. 15, 2018

(65) Prior Publication Data
US 2019/0214114 A1    Jul. 11, 2019

Related U.S. Application Data

(60) Provisional application No. 62/383,655, filed on Sep. 6, 2016.

(51) Int. Cl.
*G16H 10/20*    (2018.01)
*G06F 16/335*    (2019.01)
(Continued)

(52) U.S. Cl.
CPC .......... *G16H 10/20* (2018.01); *G06F 16/335* (2019.01); *G06Q 10/10* (2013.01); *G06Q 50/10* (2013.01);
(Continued)

(58) Field of Classification Search
CPC ........ G16H 10/20; G16H 10/60; G16H 10/00; G06F 16/335; G06Q 10/10; G06Q 50/10; G06Q 50/22
See application file for complete search history.

(56) References Cited

U.S. PATENT DOCUMENTS 7,613,620 B2    11/2009  Salwan
2003/0055816 A1*   3/2003  Paine ................. G06Q 30/02
(Continued)

OTHER PUBLICATIONS

International Search Report and Written Opinion issued by the ISA/US, Commissioner for Patents, dated Nov. 16, 2017, for International Application No. PCT/US2017/050306; 6 pages.

*Primary Examiner* — Fonya M Long
*Assistant Examiner* — Anthony Balaj
(74) *Attorney, Agent, or Firm* — Faegre Drinker Biddle & Reath LLP

(57) ABSTRACT

Methods for generating a health management template for a patient condition including retrieving a healthcare template It corresponding to a patient condition, the healthcare template comprising a plurality of data fields, populating the data fields with patient data; and generating an updated healthcare template based on a user input, wherein the user input comprises at least one of a search request or a data option selection are disclosed. Systems are also disclosed.

17 Claims, 9 Drawing Sheets

(51) Int. Cl.
*G06Q 10/10* (2023.01)
*G06Q 50/10* (2012.01)
*G06Q 50/22* (2024.01)
*G16H 10/60* (2018.01)
*G16H 80/00* (2018.01)

(52) U.S. Cl.
CPC ............ *G06Q 50/22* (2013.01); *G16H 10/60* (2018.01); *G16H 80/00* (2018.01)

(56) References Cited

U.S. PATENT DOCUMENTS

| | | | |
|---|---|---|---|
| 2006/0229932 A1* | 10/2006 | Zollo | G06Q 30/02 705/26.7 |
| 2013/0073306 A1 | 3/2013 | Shlain et al. | |
| 2013/0191161 A1 | 7/2013 | Churchwell et al. | |
| 2013/0332195 A1* | 12/2013 | Galuten | G16H 50/70 705/3 |
| 2014/0207486 A1 | 7/2014 | Carty et al. | |
| 2014/0249855 A1 | 9/2014 | Moore | |
| 2015/0066524 A1* | 3/2015 | Fairbrothers | G16H 40/20 705/2 |
| 2015/0310574 A1* | 10/2015 | Williams | G16H 40/20 705/2 |
| 2016/0110523 A1 | 4/2016 | Francois | |
| 2016/0314248 A1* | 10/2016 | Klocek | G16H 10/60 |
| 2017/0351819 A1* | 12/2017 | Yamamoto | G06F 16/285 |

\* cited by examiner

FIG. 6B

SYSTEMS AND METHODS FOR ACCESSING, COMBINING AND COLLABORATIVE FILTERING OF INFORMATION FROM MULTIPLE ELECTRONIC HEALTH RECORDS

CROSS-REFERENCE TO RELATED APPLICATIONS

This application is a U.S. National Stage under 35 U.S.C. § 371 of International Patent Application No. PCT/US2017/050306, filed Sep. 9, 2017, which claims the benefit of U.S. Provisional Application No. 62/383,655, filed Sep. 6, 2016, the entire disclosures each of which is hereby expressly incorporated by reference in its entirety.

FIELD OF THE DISCLOSURE

This disclosure relates to systems and methods for accessing, combining and collaboratively filtering of information for the same patient from one or more electronic health records and other systems. More specifically, this disclosure relates to systems and methods that provide improved ease of access and combinations of information from one or more information sources for improved patient diagnosis and treatment.

BACKGROUND

Clinicians, such as physicians, nurses and others, often struggle with retrieving and integrating information about a particular patient, context and clinical problems. While plenty of useful information is often contained in electronic health records ("EHRs") and other health information technology systems ("HIEs"), such as health information exchanges, clinicians must manually look up information in various places (often using multiple applications and screens). Retrieving patient-specific information to diagnose and/or treat a particular problem using these conventional methods and systems is thus an often slow, inefficient, cumbersome, and error-prone process.

Moreover, the volume and variety of electronic information about specific patients available to clinicians is growing by leaps and bounds. Clinicians not only have access to voluminous information from increasingly integrated electronic health records at their respective institutions, but also from elsewhere, such as health information exchanges and external EHR installations (e.g., through Epic's CARE EVERYWHERE® and Cerner's COMMONWELL™). While having comprehensive information about a patient "at your fingertips" has many benefits, information overload, especially in the presence of time constraints, is a current persistent problem. Physicians spend significant time reviewing patient information in EHRs, and cognitive overload, especially combined with other factors, may often carry a significant risk of patient harm.

Barriers to efficient and effective information retrieval systems are especially grave with certain life-threatening conditions, such as chest pain in the emergency department ("ED"). Chest pain is the second most common reason for ED visits, accounting for over seven million visits annually in the US. Evaluating chest pain in the ED is a high-risk endeavor, often with little diagnostic reward. While acute coronary syndrome or myocardial infarction (MI) are primary differential diagnoses, there are several other imminently life-threatening causes, such as cardiac tamponade and pulmonary embolism, as well as potentially life-threatening ones, such as pneumonia and esophageal rupture. However, chest pain is a rather common symptom, often with non-worrisome causes.

Proper effective treatment of a patient in the ED focuses on correctly diagnosing/treating a focused problem quickly. When patients enter the ED with chest pain, clinicians attempt to rule out imminently or potentially life-threatening causes immediately. If these life-threatening causes can be ruled out, patients are risk-stratified for the potential to have any of them. During the course of these evaluations, much information is sought. Existing evaluations or studies may impact the current evaluation and risk stratification of the patient. For instance, absent any evidence of coronary plaques, the likelihood of coronary causes decreases dramatically. Knowledge of previous tests may impact the interpretation of current ones, for instance when comparing current and old ECGs, or decisions to perform further tests. Further, in patients who have known disease, such as coronary disease, the timing and results of most recent studies often inform the prognosis and next steps.

Given the information-intensive nature of clinical work in the high-pressure, busy environment of the ED, EHR deployment has had mixed results in supporting these life-and-death decisions. Existing patient information is sometimes not accessed because it can be difficult and time-consuming to find. With the delivery of the right data at the right time and in a user-friendly format, the time often needed to obtain existing data may be reduced and the utilization of testing may also be reduced, while physicians' confidence in and satisfaction with their decisions may be simultaneously improved.

To reduce cognitive overload, increasing efficiency and effectiveness of information retrieval and review in EHRs and HIEs is important. However, conventional approaches continue to have important limitations despite demonstrated important and significant potential gains for making access to patient health information more efficient and effective. One such limitation is that the manual creation and maintenance of EHR systems is labor and time intensive, which often includes both the manual input or manual identification of data options. The manual input and/or identification of data options when collecting, assessing, and summarizing a patient's medical information can result in inconsistent and/or error-prone processes because the selection of data options typically was assessed individually by each clinician. Inconsistent and/or error-prone selection of data processes runs the risk of consistently being repeated and, thus, becoming integrated and/or unidentified in processes during diagnosis and/or treatment of the patient.

Second, conventional approaches do not scale well; solving the problem for one scenario does not save much effort for the next. In conventional systems, each user is alone; there is no relationship to what other users do or view in the system. Thus, conventional systems and methods do not allow for crowdsourcing or collective filtering and, thus, can be inefficient, time-consuming, and contain inconsistencies. Thus, systems and methods that can leverage collective user behavior to reduce data noise and filter data, within the healthcare context, are still needed.

Third, static templates are designed by EHR leadership or clinical informatics committees and then need to be implemented by IT staff, which often imparts considerable delay, and static templates do not automatically evolve to reflect the realities of clinical practice. Thus, conventional predetermined and standardized information templates can quickly become outdated as medical advances increase in various medical fields and best practices evolve. Subsequently, conventional predetermined and standardized information templates suffer from the inability to evolve with the changes in various medical fields.

Therefore, methods and systems that are more efficient, use the collective knowledge within a given medical field, diagnosis, and/or treatment to reduce human-related error, and can dynamically evolve with advancements in a given medical field are needed.

Fourth, conventional EHR systems and methods retain no memory of previous relevant information searches. A need therefore exists to make the most relevant information, at various points in time, easily accessible to the clinician, not to replicate one or more clinical "treatment scripts."

SUMMARY

Methods for generating a health management template for a patient condition, including retrieving a healthcare template corresponding to a patient condition, the healthcare template comprising a plurality of data fields, populating the data fields with patient data, and generating an updated healthcare template based on a user input, wherein the user input comprises at least one of a search request or a data option selection are disclosed.

Various aspects of this disclosure also include systems for generating a health management template for a patient condition comprising a data interface in electrical communication with a processor, a patient database, a user interface, and a template database, the user interface configured to retrieve a healthcare template corresponding to a patient condition, the healthcare template comprising a plurality of data fields, populating, by the user interface, the plurality data fields with patient data, and generating, by the processor, an updated healthcare template based on a user input, wherein the user input comprises at least one of a search request or a data option selection.

Also disclosed herein are non-transitory computer readable storage mediums bearing instructions for generating a health management template for a patient condition, the instructions, when executed by a processor in electrical communication with a template database, cause the processor to perform operations that include retrieving a healthcare template from the template database corresponding to a patient condition, the healthcare template comprising a plurality of data fields, populating the data fields with patient data, and generating an updated healthcare template based on a user input, wherein the user input comprises at least one of a search request or a data option selection.

Accordingly, the various methods and systems disclosed herein enable clinicians to easily access and combine information from one or more information sources for patient diagnosis and treatment. In various aspects, predefined and standardized information templates may combine information from an electronic healthcare record (EHR), one or more healthcare information exchanges (HIEs) and/or other systems, into a single, cohesive view of a patient's information.

The information templates disclosed herein may be focused on particular clinical contexts and/or patient conditions. Clinicians then can search one or more information sources for additional information not shown on the templates. In various aspects, the methods and systems may incorporate various passive crowdsourcing and/or collaborative filtering algorithms and, thus, clinicians can easily access information items which other clinicians have searched for/viewed in similar patient care and clinical decision making contexts. This rapid access of information items can (i) substantially increase the dissemination of best practices, (ii) substantially quicken the adoption of best-practices in a given medial field, and (iii) reduce the introduction of individual clinician error (human-error) through collaborative filtering and recommendation. In addition, the individual or collective search and viewing behavior of clinicians can be compared to clinical practice guidelines to ensure that best practices are being followed.

BRIEF DESCRIPTION OF THE DRAWINGS

The above-mentioned and other features and objects of this disclosure, and the manner of attaining them, will become more apparent and the disclosure itself will be better understood by reference to the following description of exemplary aspects of the disclosure taken in conjunction with the accompanying drawings, wherein:

FIGS. 6A and 6B show two healthcare interfaces according to various aspects of this disclosure;

Figure 1:
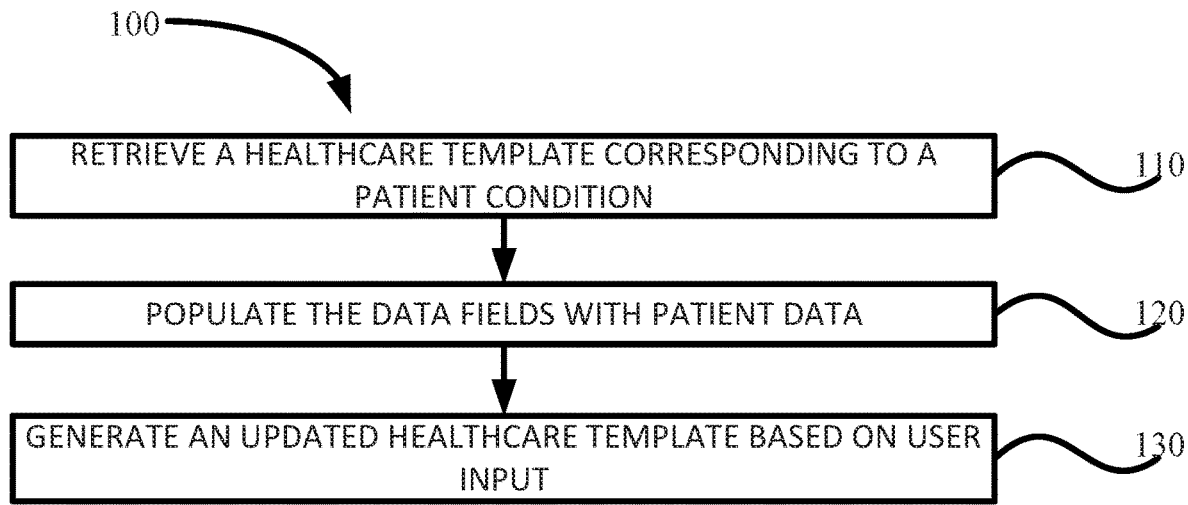
FIG. 1 is a diagram representing methods of generating an updated healthcare template according to various aspects.

Corresponding reference characters indicate corresponding parts throughout the several views. Although the drawings represent various aspects or embodiments of the present disclosure, the drawings are not necessarily to scale and certain features may be exaggerated in order to better illustrate and explain the present disclosure. The exemplifications set out herein illustrates exemplary embodiments of the disclosure, in various forms, and such exemplifications are not to be construed as limiting the scope of the disclosure in any manner.

DETAILED DESCRIPTION

The aspects disclosed below are not intended to be exhaustive or limit the disclosure to the precise form disclosed in the following detailed description. Rather, the various aspects are chosen and described so that others skilled in the art may utilize its teachings.

FIG. 1 illustrates methods for generating a healthcare template according to various embodiments. Method 100 may include retrieving a healthcare template corresponding to a patient condition (step 110). In various aspects, the healthcare template may include a plurality of data fields. The method may also include populating the data fields with patient data (step 120) and generating an updated healthcare template based on a user input (step 130). In various aspects, the user input may comprise at least one of a search request or a data option selection. In various aspects, method 100 may also include receiving data indicating the patient condition, such as symptoms such as chest or abdominal pain, or diagnoses such as hypertension and diabetes.

The generation of an updated healthcare template based on a user input is not particularly limited and may include, for example, responding to the user input being a search request by retrieving patient data corresponding to the search request. In some aspects, generating an updated healthcare template (step 130) may include (i) comparing a history associated with the search request to a criteria and adding a data option to the updated healthcare template when the history satisfies the criteria, (ii) responding to the user input being a data option selection by displaying patient data corresponding to the data option selection on the updated healthcare template, and/or (iii) comparing a history associated with the data option selection to a criteria and adding a data field corresponding to the data option selection to the updated healthcare template when the history satisfies the criteria.

The criteria is not particularly limited and may include at least one of a popularity of the data option selection request or an importance of the data option selection.

Figure 2:
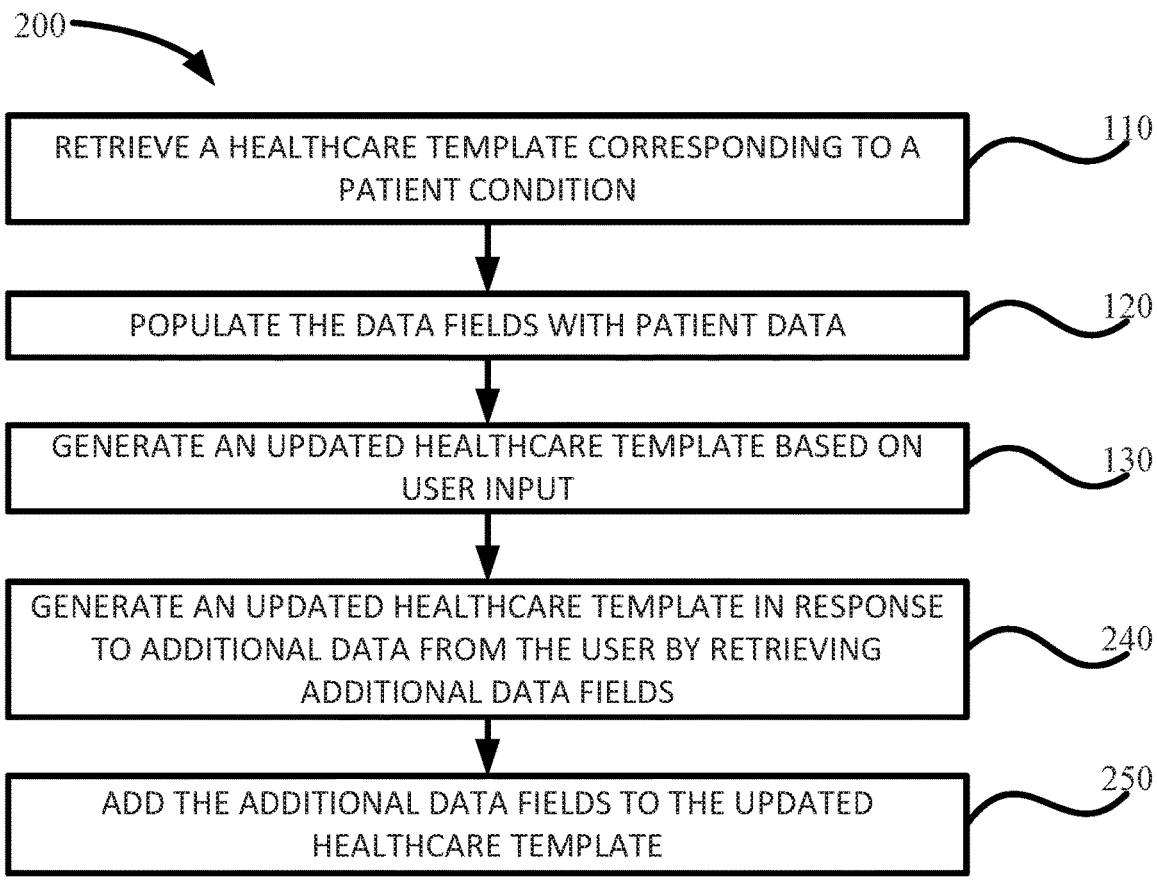
FIG. 2 is a diagram representing methods of generating an updated healthcare template by retrieving additional data fields according to various aspects.

FIG. 2 illustrates method 200 according to various aspects. Similar to method 100 of FIG. 1, method 200 may include retrieving a healthcare template corresponding to a patient condition (step 110), populating the data fields with patient data (step 120), and generating an updated healthcare template based on a user input (step 130). Method 200 may also include generating an updated healthcare template in response to additional data from the user by retrieving additional data fields (step 240) and adding the additional data fields to the updated healthcare template (step 250).

Figure 3:
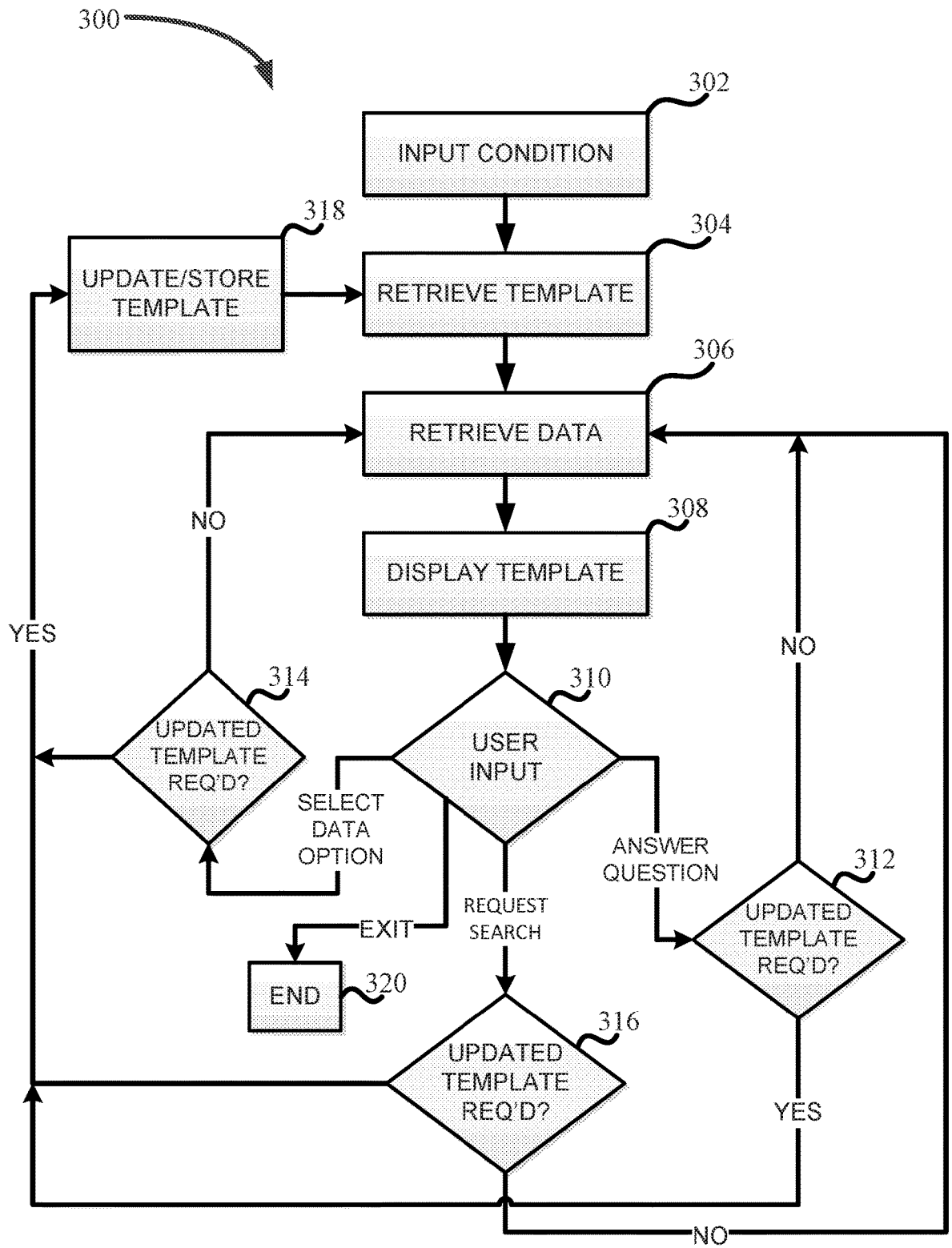
FIG. 3 is a process flow diagram according to various aspects.

FIG. 3 illustrates a process flow diagram according to various embodiments. Process 300 may include an initial input condition (step 302) that may trigger the retrieval of a template (step 304). After the template is retrieved (step 304), data may be retrieved (step 306) to populate the template. The template may also be displayed (step 308). Then in response to a user input (step 310), such as answering a question, selecting a data option, or requesting a search, a determination whether an update the template may be made (312, 314, and 316 respectively). If an update to the template is not desired (312, 314, and 316 respectively), the data may then be retrieved (step 306) and displayed in the template (308).

If the program, process, or processor makes a determination, such as through the use of collaborative filtering, that an update to the template is desired, then the template is updated and/or stored (step 318). The template is then retrieved (step 304), the data is then displayed (306) and then the template is displayed (step 308).

If there is no update or change to be made to the template and no new information is needed or requested, the program may exit and end 320.

Figure 4:
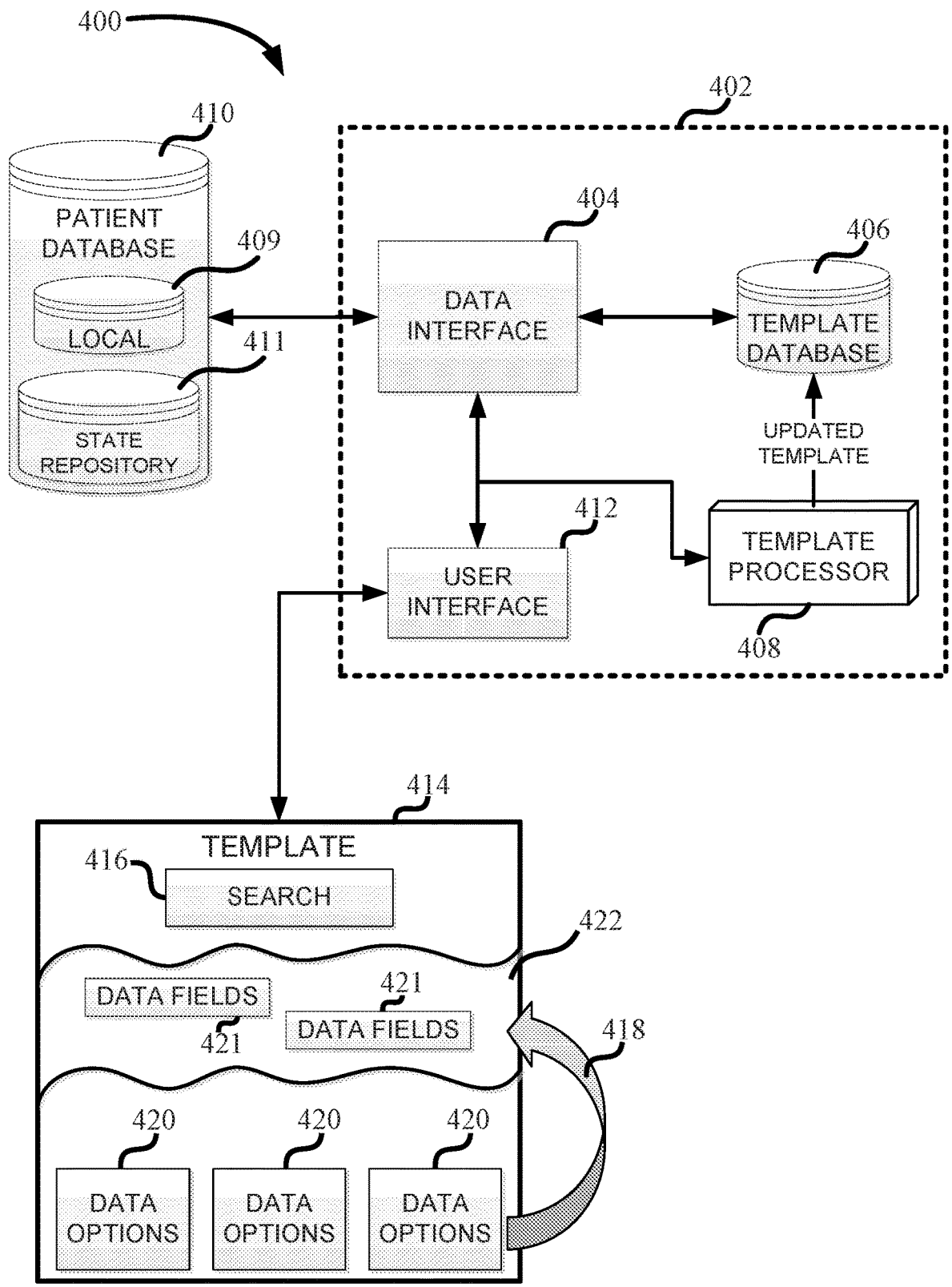
FIG. 4 is an illustrative view of a system for generating a healthcare template for a patient condition according to various aspects.

FIG. 4 contains an exemplary diagram of systems for generating a health management template for a patient condition according to various aspects. System 400 for generating a template related to healthcare for a patient condition may include a data interface 404 in electrical communication with a processor (illustrated as template processor 408), a patient database 410, a user interface 412, and a template database 406. In various aspects, data interface 404, template database 406, user interface 412 and template processor 408 may form part of a subsystem 402.

Patient database 410 is not particularly limited and may include local databases, such local database 409 or may include remote databases, such as those from health information exchanges (HIEs), exemplified by state repository database 411.

In various aspects, the user interface 412 may be configured to retrieve a healthcare template 414 corresponding to a patient condition. The healthcare template 414 may comprise a plurality of data fields 421 that may be populated (shown as 418 in FIG. 4), by the user interface 412, the plurality data fields 421 with patient data. In various aspects, the processor (e.g., template processor 408) may generate an updated healthcare template based on a user input, wherein the user input comprises at least one of a search request or a data option selection, for example, from a plurality of data options 420.

Healthcare template 414 may also comprise a search function 416 to search for one or more data options 420 to populate data fields 421 contained within an observable portion 422 of healthcare template 414.

One of ordinary skill in the art will realize that the aspects provided herein can be implemented in various configurations of hardware, software, firmware, and/or a combination thereof. Programming code according to the aspects can be implemented in any viable programming language such as C, C++, HTML, XTML, JAVA or any other viable high-level programming language, or a combination of a high-level programming language and a lower level programming language.

Processor 408 may include any suitable processing device or devices operative to execute the software/firmware. For example, processor 408 may include one or more programmable processors (e.g., central processing unit (CPU) devices), application-specific integrated circuits (ASICs), field-programmable gate arrays (FPGAs), digital signal processors (DSPs), hardwired logic, or combinations thereof.

A person of ordinary skill with the benefit of this disclosure will appreciate that clinicians or users may search the HIE using the various functions built into the template in various aspects of the systems and methods disclosed herein. In various aspects, this may add retrieved information to the template, reducing inconsistencies and error, while increasing efficiencies of obtaining, aggregating, and reviewing patient information. As many clinicians use the similar templates over time and retrieve various additional pieces of information, the original templates may be enhanced with additional information through collaborative filtering or through the removal of unnecessary or irrelevant material.

Collaborative filtering may generate recommendations for additional information items for the template. In this way, over time the original information templates may evolve into a dynamic, passive crowd-sourced information artifact that evolve with clinician behavior and clinical practice.

Accordingly, also included with the various methods and systems disclosed herein are non-transitory computer readable storage medium bearing instructions for generating a health management template for a patient condition, the instructions, when executed by a processor in electrical communication with a template database, cause the processor to perform operations comprising retrieving a healthcare template from the template database corresponding to a patient condition, the healthcare template comprising a plurality of data fields, populating the data fields with patient data, and generating an updated healthcare template based on a user input, wherein the user input comprises at least one of a search request or a data option selection.

In various aspects, the non-transitory computer readable storage medium may also include instructions for generating an updated healthcare template in response to additional data from the user by retrieving additional data fields and adding the additional data fields to the updated healthcare template.

Figure 5A:
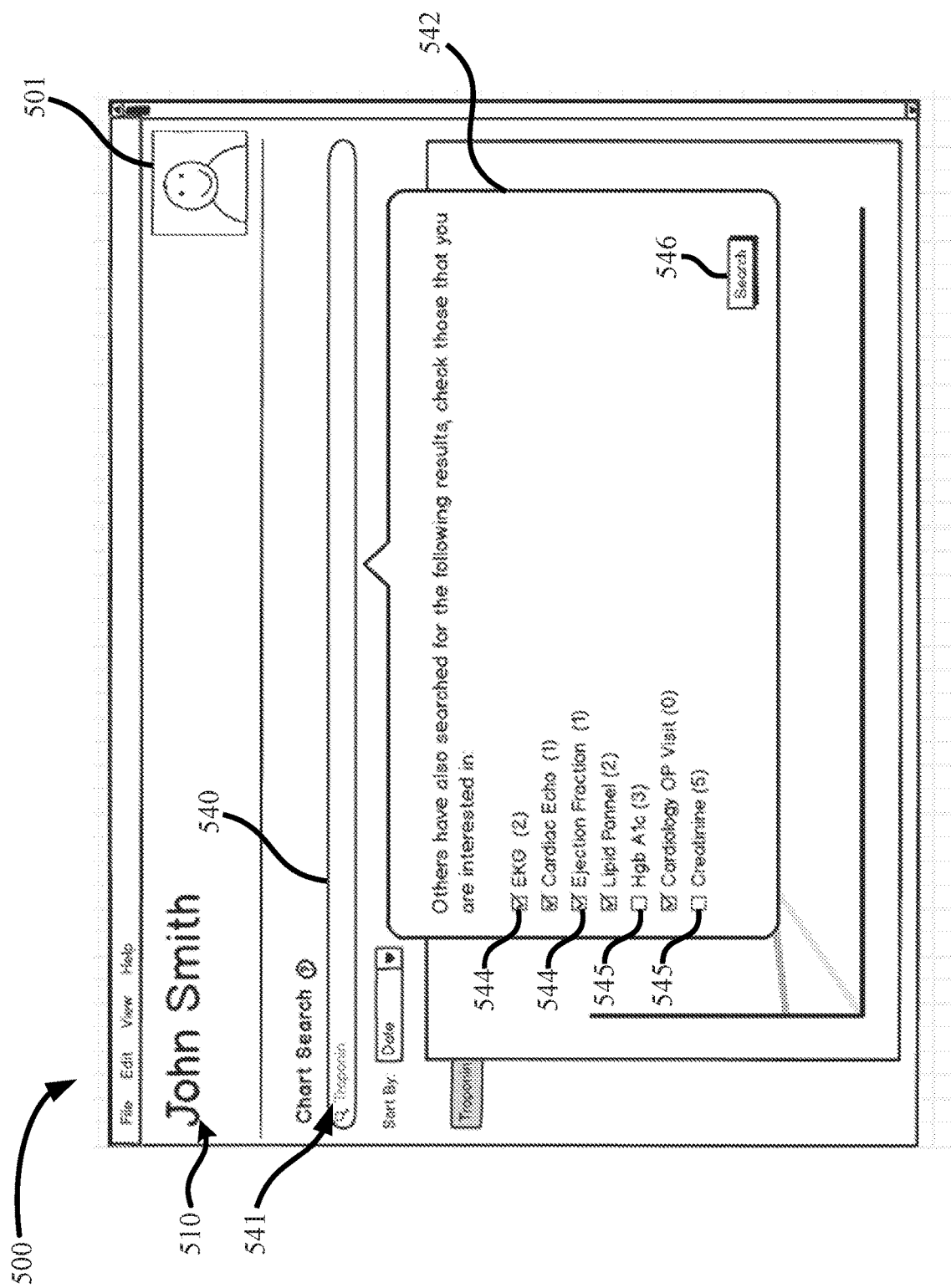
FIGS. 5A and 5B are illustrative representations of a healthcare interface according to various aspects of this disclosure.
Figure 5B:
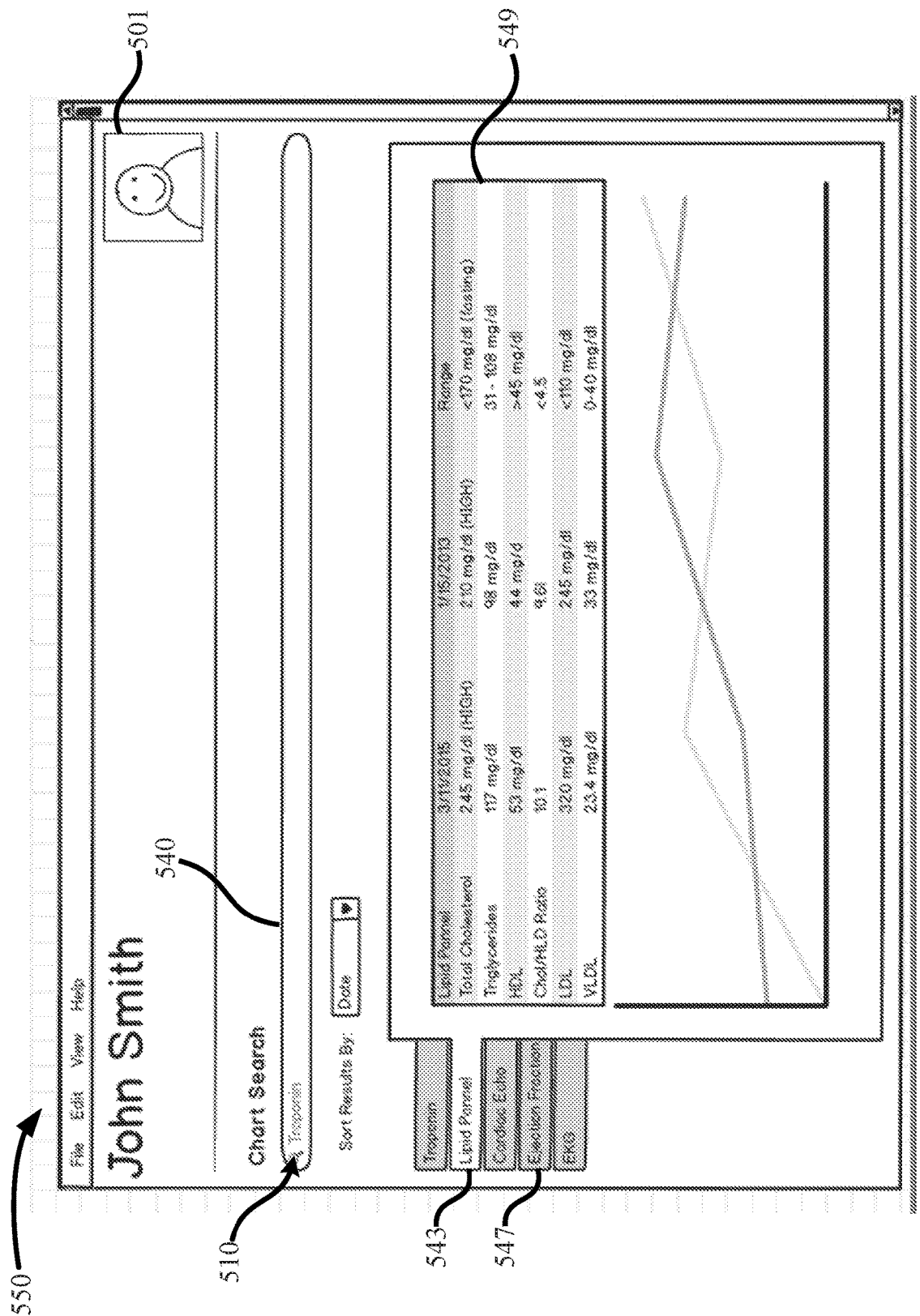

FIGS. 5A and 5B illustrate a user interface of a system implementing a non-transitory computer readable storage medium according to various aspects. Once a user (e.g., a medical doctor or nurse practitioner) logs in, the patient record may be selected or created. When a new patient record or template is created, display 500 may illustrate the patient's name 510 and a photograph of the patient 501. The user may then enter into search bar 540 a search query 541. As a search query 541 is typed into a search bar 540, as suggested results 542 may be displayed. Suggested results 542 may be changed (e.g., added or included or removed) in suggested results 542 once one or more threshold factors are met, such as through item weighting using implicit or explicit item ratings collected previously.

As used herein, the term "weighting" may include weighting the importance of an information item based on an action or non-action of a user (e.g., adding a suggested category or field, passing over a suggested category or field in order to see details). Implicit item ratings are generated when a user action indicates the user's interest in the item. Explicit item ratings are generated when the system explicitly requests that a user rate an item, e.g. through a rating request. Without being limited to any theory, it is believed that the use of weighting using implicit item ratings may allow for more robust and refined search queries, as many users may not have the time or patience to provide explicit ratings. The term "explicit weighting" may include requesting feedback from a user, such as asking them to rank the suggestions.

Moreover, in various aspects, feedback may also be voluntary or involuntary regardless of whether the feedback is implicit or explicit. For example, in some aspects, voluntary feedback may include a user's customization of personal templates, which can be a strong indicator of preference. Thus, in implicit voluntary feedback, a user's customization of personal templates can be used to suggest terms or data options to others without the user's knowledge. In explicit voluntary feedback, collaborative template editing by users or organizations (e.g., staff of a hospital, members of professional associations—such as the American Academy of Pediatrics) may not only improve the collaborative template, but may also be considered for related topics or templates. Thus, in various aspects, collaborative efforts may be analyzed and weighted with or without user's input and, thus, best-practices may be spread and adopted quickly not only within a particular diagnosis or treatment, but also within related diagnoses or treatments. Thus, not only may best practices be dispersed more quickly, but the evolution of clinical practice through focused application of best practices and evolving clinical guidelines may be accomplished with significantly less overhead.

Once suggested results 542 are populated, the user may select one or more of the suggested results. For example, selected results 544 may be populated once search 546 is activated, while unselected results 545 are not populated. The selection of selected results 544 may improve selected results 544 association with a particular template, action, or search results, while the unselected results 545 association with a particular template, action or search results may decrease through collaborative filtering.

The selected results 544 may then be displayed after selection as selected tab 543 or unselected tab 547. In various aspects, as the user selects the various tabs, information for the patient pertaining to the selected tab 543 may be populated as selected patient data 549.

Figure 6A:
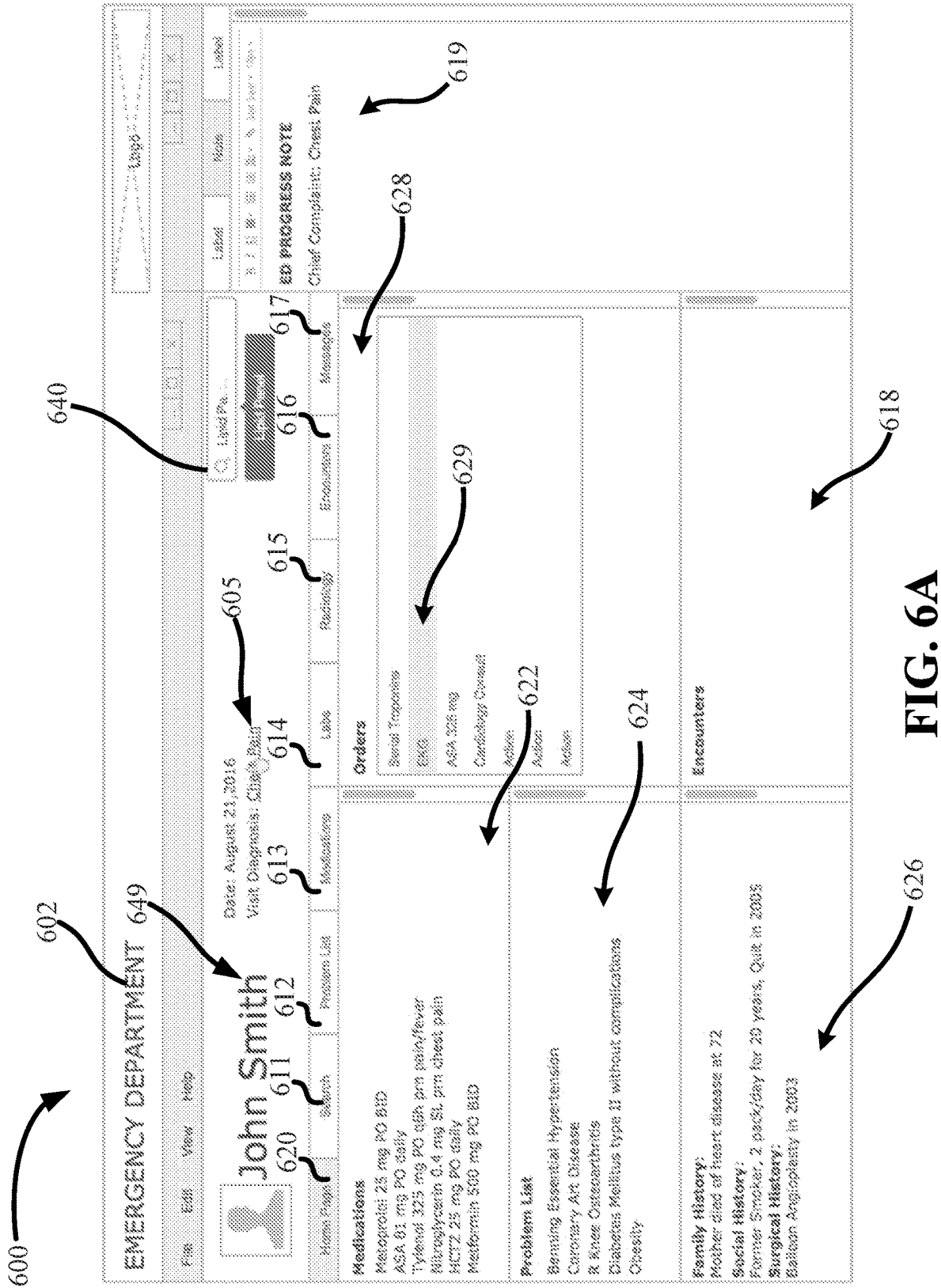
Figure 6B:
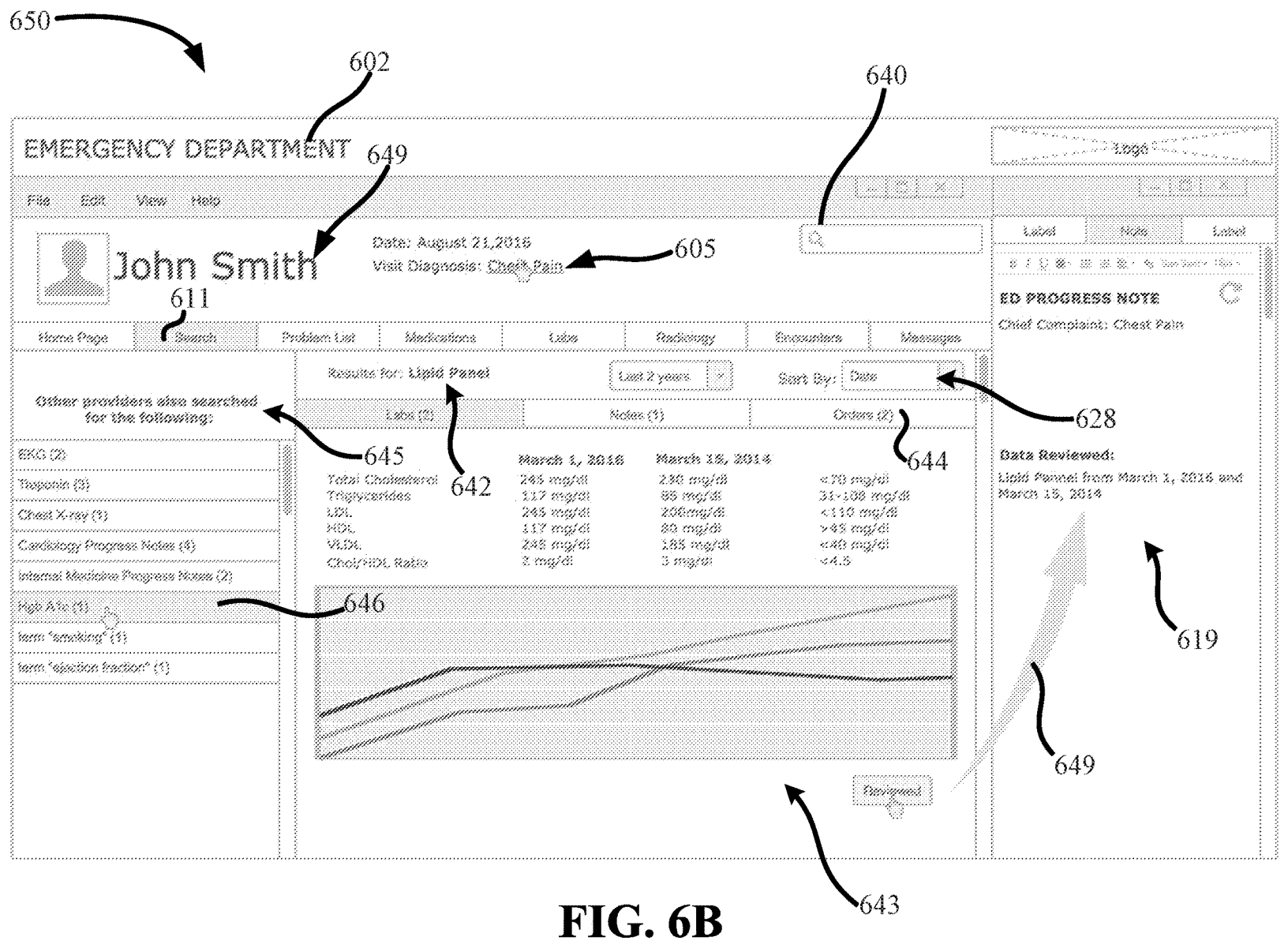

FIGS. 6A and 6B are screenshots of one aspect of a system implementing and aspect of a method described herein. Screenshot 600 may display the title or association of a particular template, such as the exemplified emergency department template 602. The patient's name 649 may be displayed along a various tabs and the purpose of the diagnosis, such as visit diagnosis 605, which may be found with search bar 640 and may be the chief complaint from the visit and/or the most urgent (e.g., based on various triage criteria). Home page tab 620 may include one or more windows such as a medications window 622 showing the medications the patient has taken, a problem list window 624 listing diagnoses or illnesses, which may be based—at least in part—on the visit diagnosis 605, and family history window 624 that lists known illnesses in the family. The orders window 628 may list orders already requested or may suggest various orders, such as EKG order 629. Also, encounters window 618 may list summaries of encounters between medical professionals and the patient.

Additional tabs include search tab 611, problem list tab 612, medications tab 613, labs tab 614, radiology tab 615, encounters tab 616 and messages tab 617. In various embodiments, the tabs may be color coded to provide notification to the user's that the tab has recently been updated with new data options or with new data (e.g., a new lab report has arrived).

Moreover, the home page or other various tabs may also include other pertinent patient information, such as legal orders (e.g., a do-not-resuscitate DNR order, restraining orders), related religious affiliation information (e.g., local clergy contact information, religious medical restrictions), contact list (e.g., emergency contact information, guardianship information), organ donor information, allergy information, psychological information (e.g., whether the patient is suicidal or a potential harm to others), insurance information, and pharmacy information.

FIG. 6B contains screenshot 650 where the search tab 611 is activated. When search tab 611 is activated, suggested search window 645 showing suggested search options 646 may be shown. As described in detail above, the suggested search options may be provided through the aid of collaborative filtering, such as when a user selects search option 646. Moreover, once the search is made, such as lipid panel search 642, patient data associated with the search 643 may be displayed. Orders associated with the search may be reviewed with the orders tab 644 and once the data is reviewed, the user may send the review record 649 to the ED progress notes 619 to help capture the complexity of the visit.

Without being limited to the specific aspects disclosed herein, it is believed that the various display of tabs and windows of various template may support medical-decision making by providing concise, context sensitive, real-time data while simultaneously uncluttering the process by extraneous information. By incorporating collaborative filtering with the customization of electronic health records (EHRs), information flow and adjustment for context, environment, and user preferences may be accommodated.

Thus, the methods and systems disclosed herein provide mechanisms for clinicians, such as physicians, nurses and others, to easily access and combine information from local EHRs and health information exchanges (HIE) for patient diagnosis and treatment. Predefined and standardized information templates may combine information from an EHR, and one or more HIEs, in a single, cohesive view of a patient's information. The information templates may be focused on particular clinical contexts and/or patient conditions in various aspects. Clinicians can search the HIE(s) for additional information not shown on the templates. Moreover, through a crowdsourcing and/or collaborative filtering algorithms, users can easily access information items which other clinicians or users have searched for/viewed in similar patient care and clinical decision making contexts.

This rapid access of information can (i) substantially increase the dissemination of best practices, (ii) substantially quicken the adoption of best-practices in a given medial field, and (iii) reduce the introduction of individual clinician error (human-error) through collective filtering and recommendation.

Moreover, in various aspects, this may be done passively in the background reducing resources required while simultaneously improving clinician efficiency.

EXAMPLES & DATA

The Indiana Network for Patient Care (INPC), Indiana's major health information exchange, offers clinicians access to the most complete, cross-facility virtual electronic patient record in the nation. Implemented in the 1990s, the INPC collected data from over 140 Indiana hospitals, laboratories, long-term care facilities and imaging centers. It contained over 3.5 billion clinical results, 80 million radiology images, 50 million text reports and 750,000 EKG readings, and handled nearly three million health transactions daily. The INPC stored close to 100% of the patient information for most patients, especially those in the Indianapolis metropolitan area, where the intervention sites for the following example according to various embodiments was located. CAREWEB®, the Web-based information viewer for the INPC, was integrated with the example as described below.

Contextual observations of information management in two deployment sites (Indiana University Health Methodist Emergency Department and Eskenazi Health Emergency Department) demonstrated the importance of integrating existing information from the INPC in the clinician's workflow. Seven residents and attending physicians were observed for a total of 17 hours during their daily work in the high acuity/trauma area. All searches were recorded for information both in the EHR and using an embodiment that incorporated the user interface of CAREWEB®, the item(s) sought were logged, and the pathway of retrieval was documented. Of the total 70 encounters observed, nine involved chest pain. In discussions with clinicians after the observations, providers indicated that the information in CAREWEB® was extremely important for medical decision-making. However, logistical issues, such as login problems and the time required to find information, often kept clinicians from using CAREWEB®.

Figure 7:
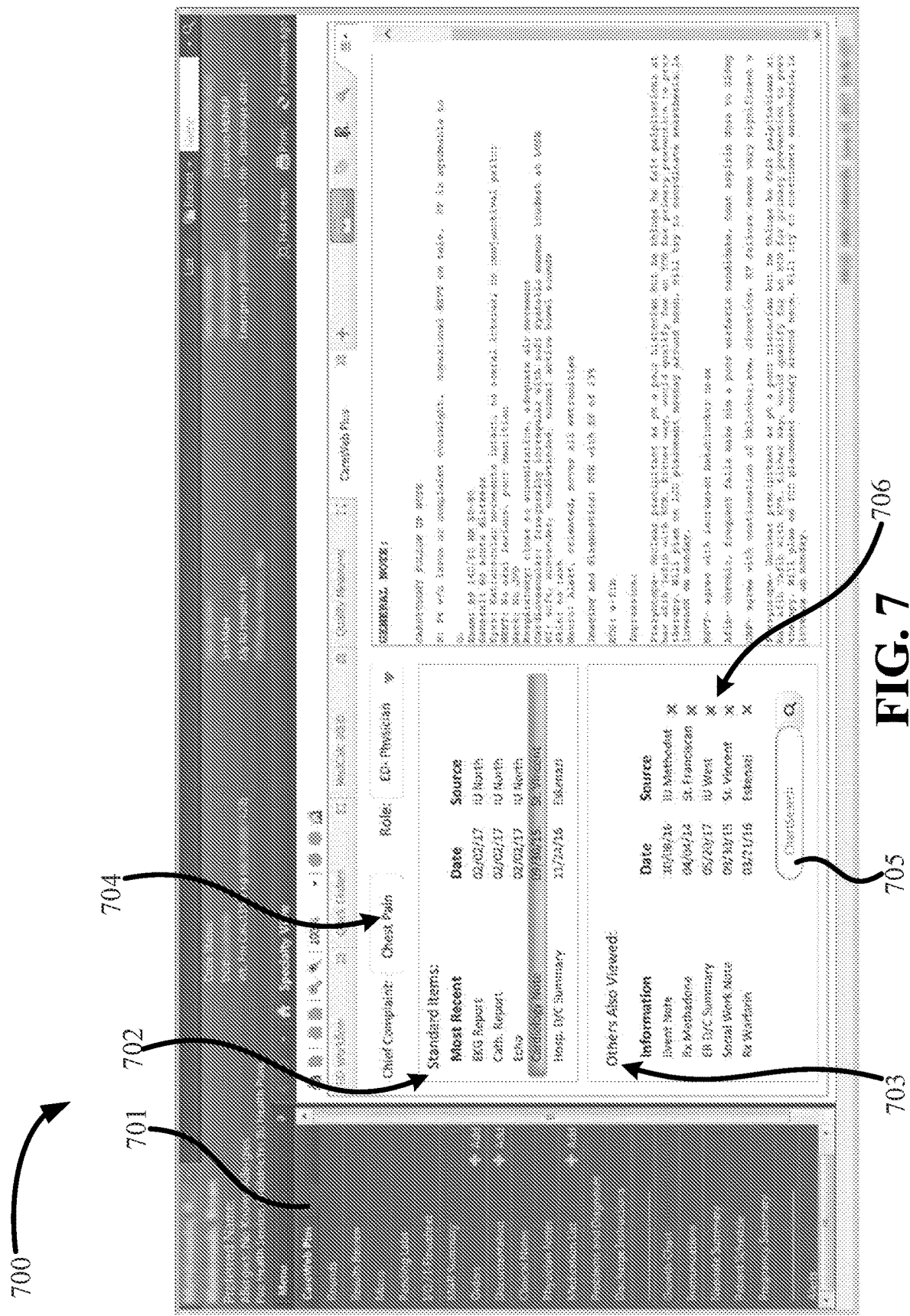
FIG. 7 is a screenshot of an exemplary healthcare GUI that uses collaborative filtering according to various embodiments.

The purpose of the embodiment that incorporated CAREWEB®Plus, as shown in FIG. 7, was to put relevant information items from the INPC at the clinician's fingertips within the EHR environment. Some improvements to functionality included incorporating an exemplary embodiment into the existing user interface of CAREWEB®Plus shown in FIG. 7: The user invoked CAREWEB®Plus through the navigation menu on the left (740). (For this example, CAREWEB®Plus incorporating the embodiment shown was only be available if the chief complaint is chest pain.) The CAREWEB®Plus tab displayed Standard items and Others also viewed sections. Standard items (further described below) were predefined, static information items specific to the Chief Complaint. The "others also viewed" was a list of recommendations generated by an exemplary collaborative filtering (CF) algorithm according to various embodiments (described in further detail below). The user was able to change the Chief Complaint, if necessary, to generate an information display for a different problem. If a relevant information item was not displayed in either "Standard Items" or "Others Also Viewed", the clinician was able to use "Search" to retrieve additional data from the traditional CAREWEB® application, generating an input for the exemplary CF algorithms. Selecting and viewing a recommendation was used as positive feed-back for the exemplary CF algorithm, removing one (using the "x") was used as negative feedback.

Standard items of CAREWEB®Plus in a collaborative project among Regenstrief Institute, Indiana University Hospital and Indiana Health Information Exchange (IHIE) was implemented. The list of Standard items was developed from the ED observations and consultations with ED clinical leaders. It included the most recent EKG, ECHO, catheterization report, cardiology note and discharge summary. The SMART-on-FHIR architecture provided improved flexibility in implementing the example with other EHRs.

In some embodiments, CAREWEB® search log data may improve collection of and supplement existing log data. Existing log data may include items such as Timestamp, Search Text, Data Category, Date Range Constraint, Patient and Number of Results. Searches were or may be logged both on the client and the server, with slightly different sets of data. In this example, missing data elements to the respective logging functions were added. For instance, the user ID for the user interface portion, but not the server portion of search logging was captured.

Also, in some embodiments, it may be desirable to establish the boundaries of a single search session with increased certainty (e.g., for all search requests performed by a user searching for data on a specific patient during the same encounter). Additional data from the client logs may be extracted, in some embodiments, to determine the interval of time that a given patient's record was viewed, allowing the grouping of search activity into discrete sessions. In various embodiments, a table of synonyms (for example, here the table of synonyms that CAREWEB® used internally) may be used to determine which search terms are equivalent (such as EKG, ECG and electrocardiogram) during search log processing.

Additionally, in the example here, data derived from the logs with data from other sources was supplemented. Relevant patient (such as details of the emergency department encounter, diagnostic test results, prescribed medications and comorbidities) was extracted and provider data (demographics and specialty status) from the INPC was also extracted.

Here, the exemplary design of CAREWEB®Plus (for example, as shown in FIG. 7) underwent initial evaluation with representative ED users. It was found that the design was user-centered and allowed for an agile development processes with only ten ED physicians. In various embodiments, standard human-computer interaction methods may be employed, including heuristic evaluation, usability testing, cognitive walk-throughs, and/or keystroke-level modeling—as appropriate.

It should be recognized that a person of ordinary skill—with the benefit of this disclosure—may further use or adapt various user-centered design process or systems when addressing nuances for implementation of the various embodiments disclosed herein. These may include the best modalities to display recommendations, the clinical workflow that may influence what recommendation(s) should be made, optimal methods for collecting implicit and/or explicit ratings for recommendations, and circumstances under which recommendations may not be appropriate.

Clinicians' Search Terms Related to Chest Pain Cluster

Figure 8:
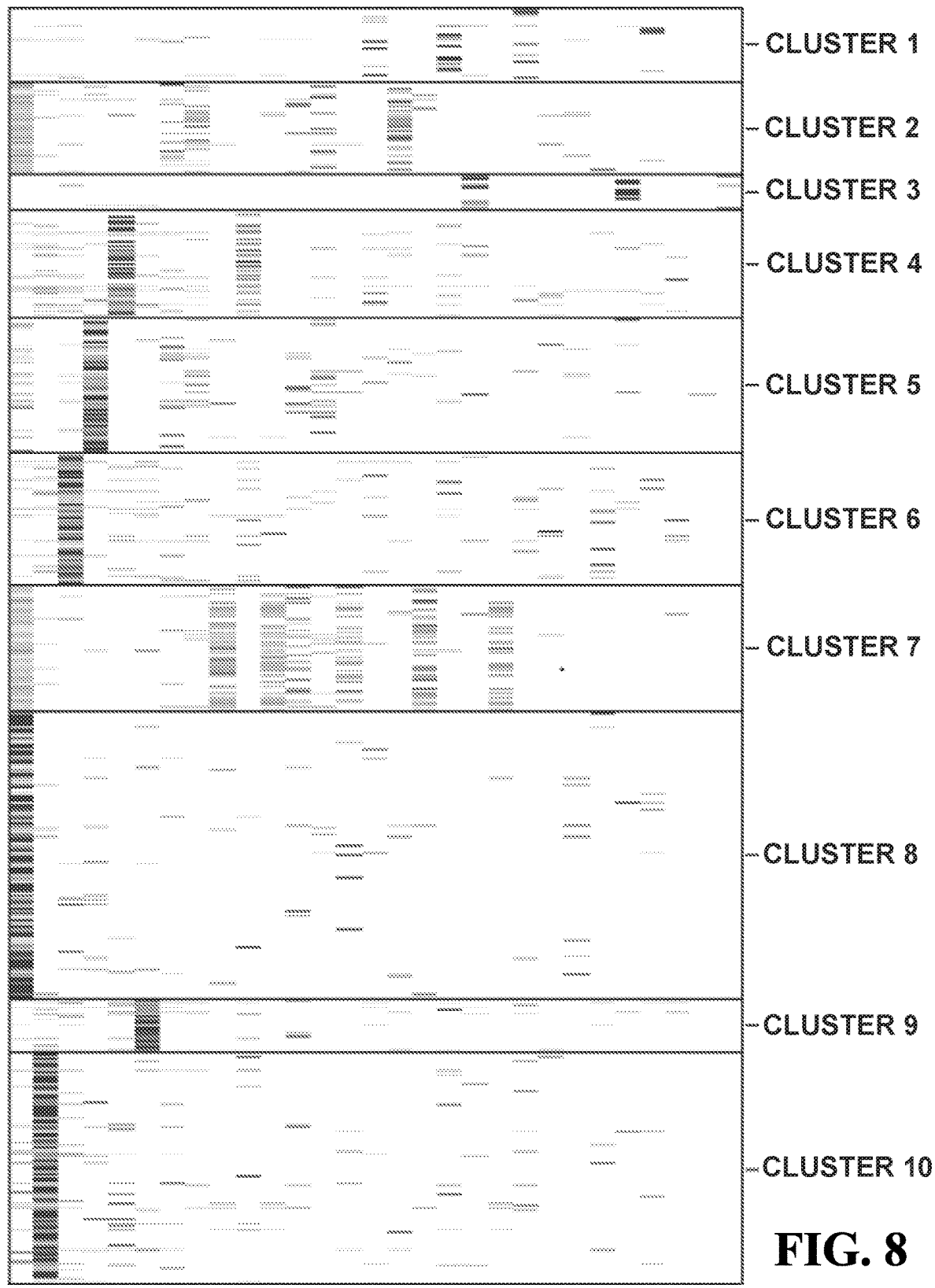
FIG. 8 shows representative cluster data for term searches and the frequency of such search terms.

Data was collected and analyzed from 2,926,932 searches over about four years for about 4,500,000 patients with about 108,000 unique search terms. Patterns were analyzed among patients and search terms about them. In the particular data representation in FIG. 8, search sessions that contained at least one term related to cardiovascular disease, such as "EKG", "Troponin" and "cardiol" were analyzed. For 43,638 patients, there were 178,424 lcardiac-related and 550,831 non-cardiac related searches. Each patient was represented as a vector of search term frequencies. Term frequencies across all search terms were calculated, not just those related to chest pain, and clustered patients with respect to their search term frequencies. FIG. 8 shows the results for clustering 43,638 patients into 10 patient clusters. This exemplary data helps show that clustering structures exist among patients and search terms and, according to various embodiments, may be used to characterize patients.

Thus, FIG. 8 helps to show that collaborative filtering algorithms—with the benefit of this disclosure and according to various embodiments disclosed herein—may be adapted to medical information retrieval; which beforehand has not been possible. In some embodiments, the CF algorithms in medical information retrieval may differ from conventional CF algorithms (e.g., ones used in ecommerce) in one or more of the following ways:

In some conventional CF algorithms, rich meta-information about products, such as descriptions and images, user reviews and ratings, and users, such as social network relations and user profiles, is typically available. Such meta-information enables sophisticated content-based CF algorithms that leverage the inherent characteristics/properties of products and users.

Unfortunately, similarly rich meta-information is not typically available in healthcare. Thus, in some embodiments, CF algorithms may be able to leverage or account for the relations among patients, physicians and patient-physician interactions, and thus be able to produce helpful recommendations.

Also, some conventional ecommerce algorithms may rely on latent factors or factors that are hidden in and inferred from data. Such latent-factor methods typically only achieve superior performance in predicting ratings, but not necessarily in recommendations. A more serious issue with conventional latent-factor methods is that the meaning of the factors is unknown and cannot be explicitly interrelated. In some embodiments, the CF algorithms, on the other hand, are able to explain recommendations by reasoning back to patient and/or physician similarities, as well as communicating their dynamics over time. Thus, some CF algorithms according to various embodiments, may be intuitive, interpretable, and/or verifiable—a currently unfulfilled need in medical decision support systems for more than thirty years.

While some conventional patient similarity measurements, such as those based on metric learning, tend to be theoretically elegant, they may have poor performance due to computational complexity. However, here CF algorithms, according to various embodiments, may be computationally lightweight and inexpensive, and thus better suited for real-time applications, such as in an ED of a medical center.

In some embodiments, CF algorithms and methods may account for various factors. For example, past behavior of physicians may be assumed to be a reasonable approximation for the appropriate level or standard of care and, therefore, CF recommendations in various embodiments may initially be based on these behaviors; behaviors that are expected to be clinically useful.

Also, patients may share commonalities and similar patients may stimulate similar information retrieval patterns by physicians. This has been validated through the examples descried herein work described above. Thus, a person of ordinary skill, with the benefit of this disclosure, may expect some CF algorithms or methods to produce recommendations based on patient and physician commonalities that are clinically relevant.

For example, to recommend relevant and context-specific information items about a patient "pt" to a physician "phy," an exemplary CF method disclosed herein had four major components:

Component 1: identification of pt's "similar" patients (denoted as "Nearest Neighbor of the patient" or NNbr (pt)) and phys' "similar" physicians (denoted as "Nearest Neighbor of the physician" or NNbr(phys)). The rationale was that a physician is likely to search for similar terms when seeing a patient who resembles previous patients. In addition, physicians caring for the same patient in the ED, and those of similar status and/or with similar search intentions are mostly likely interested in similar information. The most frequent search items from NNbr(phys) over NNbr(pt) were considered as initial candidates for recommendation in this example.

Component 2: utilization of sequential patterns among the search terms from NNbr(phys) over NNbr(pt). Recommendation candidates were prioritized based on terms that have the highest likelihood of being searched next following a specific term. For instance, after a physician has searched for an existing echocardiogram, other items of likely interest are often findings from cardiac catheterizations.

Component 3: integration of physician feedback on previous recommendations. Candidate information items, which received positive feedback, either from the specific physician phy or others, were ranked higher for recommendation. Recommendation candidates were regenerated if physician feedback indicated a different search intention/direction. For instance, when a physician changed the Chief Complaint, for example, as shown in FIG. 7, the CAREWEB®Plus compliant graphic user interface ("GUI") updated the set of recommendations.

Component 4: elimination of items that are on the "standard items" list. As described in Section C.2.1.2, CAREWEB®Plus included a set of "standard items", which was a group of information items related to the chief complaint under consideration. Items on that list did not appear in the list of recommendations.

These four components generated a (new) list of recommended information items in response to a physician action, such as reviewing a recommended information item, performing a new search query and generating feedback on a recommendation.

Patient similarities were calculated from search logs generated during patients' ED visits and other relevant information about patients. Patient similarities were measured using information such as diagnosis codes, demographic information and medication records extracted from EHRs. Patient similarities generated in this manner were generic and not specific to ED scenarios. Search logs revealed that the information items that physicians are particularly interested in during ED visits and thus identify the most ED-relevant patient information. Thus the ability of various embodiments described herein demonstrated the feasibility of using Search Term Frequencies (denoted as pSTF) from search logs in characterizing patients. In addition to pSTF, three other sets of variables extracted from search logs were incorporated: Static Information and Summary Statistics (pSSS), Test Result Indicators (pTRI) and Temporal Search Sequences (pTSS). Patient similarities were calculated from each of the four variables independently and the resulting similarity measures were aggregated into a single patient similarity value. The four variables and their similarity measurements were:

1. Patient Search Term Frequencies (pSTF): Each patient was represented using a vector of his search term frequencies. Term frequency inverse document frequency (tfidf) conversion was applied to properly weigh different terms. Cosine similarities ($\cos_{pSTF}$) were calculated over the weighted pSTF variables to measure patient similarities over pSTF.

2. Patient Static Information and Summary Statistics (pSSS): pSSS included variables such as 1) demo-graphic information; 2) chief complaint(s), medication history and disease profile; 3) the average number of search terms during all ED visits of the patient; 4) the percentage of ED visits that resulted in admission; and 5) specialty and status distributions of the physicians who have seen the patient. These variables were aggregated over the entire patient's ED visits to reflect the patient's general health status and health care utilization. Cosine similarities were also used as the similarity metric ($\cos_{pSSS}$) over pSSS vectors.

3. Patient Test Result Indicators (pTRI): Searches on lab tests in CAREWEB® return were either numerical or categorical test results. These results were converted to categorical values such as normal, abnormal and N/A based on their respective criteria. A pTRI vector was constructed for each patient, each dimension corresponding to one of his most recent chest pain-related lab test results. For pTRI, a modified Jaccard coefficient was defined, which calculated the ratio of common test results between two patients. When the trend of a series of lab test results matters, as for instance in the case of troponin, several dimensions in the pTRI vector were allocated to the test series and a sequence-alignment based scoring function was defined to measure the trend similarity and add it to the Jaccard coefficient. This coefficient was used as the similarity measurement (jaccad$_{pTRI}$) for pTRI.

4. Patient Temporal Search Sequences (pTSS): For each patient pt, their significant ED visits were represented using a set of search sequences, each sequence consisting of search terms in order and the time intervals in between during one such ED visit, that is, $$S^i = \{s_j^i = s_{j1}^i, \Delta t_{j1}^i s_{j2}^i, \Delta t_{j2}^i, \ldots, \Delta s_{jn}^i\}$$
$$[j=1, \ldots, n_i]$$

where $n_i$ is the number of $pt_i$'s j-th visits, $s_j^i$ is the search sequence for $pt_1$'s j-th ED visit, $s_{jk}^i$ is the k-th search term in $s_j^i$, and $\Delta t_{jk}^i$, is the time interval between $s_{jk}^i$ and $s_{j(k+1)}^i$. Search term synonyms and misspellings were handled by existing programming logic in CAREWEB®. Time granularity was set to seconds. These search sequences captured the search dynamics for each patient. Also, the ordering and time intervals between search terms encoded the underlying reasoning process for diagnostic decision making. For pTSS, a normalized sequence-wide similarity (sa$_{pTSS}$) was devised to compare two search sequences. The approach was based on the ideas from sequence alignment in bioinformatics. It highly scored and, thus, promoted the alignment of the same search terms and similar time intervals between these terms. Therefore, similar sequences (with similar search terms and similar time intervals in between) were aligned well and, thus, had a high alignment/similarity score. The score was normalized by self-alignment scores, and used as the similarity sa$_{pTSS}$ between $s_j^i$ and $s_q^P$. The similarity (maxsa$_{pTSS}$) between two patients under pTSS were calculated as the maximum of pairwise sa$_{pTss}$ similarities between the two sets.

Aggregated patient similarity: the four similarities were aggregated in a linear fashion into an overall measure of patient similarity (ptSim):

$$\text{ptSim} = \frac{1}{2}(\cos_{pSTF} + \cos_{pSSS} + \text{jaccard}_{pTRI} + \text{maxsa}_{pTSS})$$

Similarly, physician similarities were calculated from several information sources, such as information about the physicians themselves and the patients they have seen. Methods for physician similarity measurement often use specialty, years of training/experience and status, which may be aggregated by patient care and information retrieval activity. Specifically, two sets of variables were extracted and used: Physician Status Information and Summary Statistics (ySSS), and Physician Patient Lists (yPTL). Physician similarities were from each of the two sets of variables separately and combine them in a Physician Similarity Hierarchy (PSH). The physician variables and their respective similarity measurements were as follows:

Physician Status Information and Summary statistics (ySSS): The ySSS variables included 1) years of training/experience in ED and current status; 2) specialty and/or board certification status; 3) the number of patients the physician has seen in the ED; 4) the number of patients admitted by the physician; and 5) search term distributions over patients. These variables collectively represented the experience of physicians in the ED. Cosine similarities were used as the similarity metric ($\cos_{ySSS}$) over the vectors of ySSS variables.

Physician Patient Lists (yPTL): For each physician phys$_i$, generated a list of $n_i$ patients who the physician has seen in a certain period of time. Physician similarity (ens$_{yPTL}$) was calculated from yPTL by assembling pairwise patient similarities from the list using an ensemble operator.

Aggregating Physician Similarity: Physician similarities and ens$_{yPTL}$, were combined into a single measure of physician similarity (physSim) as follows:

$$\text{physSim} = \frac{1}{2}(\cos_{ySSS} + \text{ens}_{yPTL}).$$

The physicians based on physSim were then clustered into a hierarchy PSH. Intuitively, physicians with different status and experiences fell into different levels in PSH. The recommendations for junior physicians were generated by leveraging the experience of senior physicians in PSH. This helped to facilitate the ability to weigh recommendations by physician experience, which is very important in some settings, such as teaching hospitals.

Generating recommendations: After a patient pt$_j$, was assigned to a physician phys$_i$, an initial list of information items $$R_0^{ij}(r_{o1}^{ij}, r_{o2}^{ij}, \ldots, r_{oK/2}^{ij})$$

was generated and recommended for phys$_i$ when viewing the chief complaint information for pt$_j$. After that, upon each search or review action of phys$_i$ on pt$_j$, a new, sorted list of recommended information items $R_t^{ij} = (r_{t1}^{ij}, r_{t2}^{ij}, \ldots, r_{tK/2}^{ij})$, t=1, 2, . . . was generated and displayed. To facilitate the generation of recommendations, physician $phys_i$'s top-M (e.g., M=10) most similar physicians ($NNbr(phys_i)$) (in terms of physSim) were identified first. These similar physicians included those from different experience levels of PSH, for example, if $phys_i$ is junior, then ($NNbr(phys_i)$) included senior physicians, by exploring the PSH structures starting from $phys_i$. Then, patient $pt_j$'s top-N (e.g., N=50) most similar patients ($NNbr(phys_j)$) (in terms of ptSim) were identified. The set ($NNbr(pt_j)$) may be empty ($NNbr(pt_j)$)=θ), for instance if the patient $pt_j$ is new to the system. A local Markov chain model $MCM_{local}$ was built from the search terms on $NNbr(pt_j)$. As used herein, a Markov chain can be understood to include a statistic model that represents transition probabilities among terms. If NNbr $(pt_j)$=Ø, then $NNbr(phys_i)$). $MCM_{local}$ captured the context-specific search term transitions, and thus their sequential patterns, that occur among similar patients. A raw set of recommendation candidates was first constructed and then subsequently refined into a set of final recommendations. The refinement was based on the feedback from similar physicians $NNbr(phys_i)$ on previous recommendations. For each patient, feedback was tracked and aggregated on each recommendation by all physicians. Each recommendation had three associated feedback counts, representing the cumulative number of positive/negative/neutral feedback instances.

Initial recommendations: The top-K (e.g., K=10) most popular information items that physicians in $NNbr(phys_i)$ searched with regard to patients in $NNbr(pt_j)$ was the initial recommendation candidates $C_0^{ij}$. If physicians in NNbr $(phys_i)$ never search for information about patients in NNbr $(pt_j)$, the top-K most popular information items for patients in $NNbr(pt_j)$ were used as $C_0^{ij}$. If $NNbr(pt_j)$=Ø, the top-K (e.g., K=10) most popular information items from the physicians in $NNbr(phys_i)$ were used as $C_0^{ij}$. Recommendation candidates were sorted based on 1) their popularity and 2) aggregated feedback. The top-ranked K/2 candidates were used in $R_0^{ij}$ and recommended to physician $phys_i$. If the patient similarities from $NNbr(pt_i)$ are statistically smaller than average, the exemplary system indicated that it did not have enough similar patients to make recommendations.

Subsequent recommendations: Once physician $phys_i$ reviewed a recommended information item $r_{t-1,\ k}^{ij}$, the search terms that are most likely to follow $r_{t-1,\ k}^{ij}$ based on the Markov chain $MCM_{local}$ were used to generate follow-on recommendation candidates ($C_t^{ij}=(r_{t1}^{ij}, r_{t2}^{ij}, \ldots, r_{tK}^{ij\prime})$). Meanwhile, positive feedback was accumulated for $r_{t-1,\ k}^{ij}$. For example, if the physician $phys_i$ initiated a new search $s_{j,\ t-1}^t$ outside of previous recommendations, $C_t^{ij}$ was identified from $MCM_{local}$, if $s_{j,\ t-1}^t$ was contained in $MCM_{local}$. Physicians' feedback on $C_t^{ij}$ was integrated as weights to re-rank all the recommendation candidates. The two ranking lists $C_t^{ij}$ and $R_{t-1}^{ij}$ were joined into ranking list $R_t^{ij}$ for next recommendations.

Capturing search intention and context: In some embodiments, it may be important to understand what physicians are looking for in what context in order to generate accurate recommendation. In the exemplary case, if $s_{j,t-1}^t$ was not contained in $MCM_{local}$, it indicated that the search starts a new direction that was not captured by the current CF content. In this case, the initial recommendations were regenerated after replacing similar patients $NNbr(pt_j)$ by the top most similar patients that have the search term $s_{j,\ t-1}^t$ and replacing similar physicians $NNbr(pt_j)$ who searched the term $s_{j,\ t-1}^t$. $MCM_{local}$ were updated correspondingly.

In some instances, for example, it may be difficult to capture the real context of search activities, because the current system cannot log any offline activities among physicians and nurses, the search/click patterns of the physicians may be leveraged to infer context. For example, if a physician has been clicking on quite a few items after a single recommendation and spending sufficient time on certain items, it could be a good indication that he is looking for very specific information. Thus, specific information items in the recommendations were reweighted higher. In some embodiments, specificity may be roughly quantified by the frequencies of the search terms.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," "one aspect," "various aspects" etc., indicate that the embodiment or aspect described may include a particular feature, structure, or characteristic, but every embodiment or aspect may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for generating a health management template for a patient condition, comprising:
    retrieving a healthcare template corresponding to a patient condition, the healthcare template comprising a plurality of data fields;
    populating the data fields with patient data; and
    presenting a user interface including both a search request selection and a data option selection;
    receiving user input comprising selection of one of the search request or the data option;
    generating an updated healthcare template based on the user input comprising a search request selection, comprising:
        identifying in one or more databases a set of plurality of similar physicians having similarities to the user;
        identifying in the one or more databases a set of a plurality of similar patients having similarities to the patient;
        generating and displaying a first list of recommended information items based on collaborative filtering of information in the one or more databases associated with the set of similar physicians and the set of similar patients;
        receiving user input after displaying the first list of recommended information items, wherein the user input includes at least one of (1) a selection of an information item on the first list, or (2) a search term outside of the information items on the first list;
        generating and displaying a second list of recommended information items in response to the user input representing the selection of an information item from the first list, wherein the second list of recommended information items is based on the selected information item from the first list, and collaborative filtering of the information in the one or more databases associated with the set of similar patients and the set of similar physicians; and
        generating and displaying a third list of recommended information items in response to the user input representing the selection of the search term outside of the information items on the first list, wherein the third list of recommended information items is based on the search term outside of the information items on the first list, and collaborative filtering of the information in the one or more databases associated with the set of similar patients and the set of similar physicians; and
    generating an updated healthcare template based on the user input comprising a data option selection, comprising:
        comparing a history associated with the data option selection to a criteria, wherein the criteria comprises at least one of a popularity of the data option selection request or an importance of the data option selection; and
        adding a data field corresponding to the data option selection to the updated healthcare template when the history satisfies the criteria.

2. The method of claim 1, further comprising receiving data indicating the patient condition.

3. The method of claim 1, further comprising generating an updated healthcare template in response to additional data from the user by retrieving additional data fields and adding the additional data fields to the updated healthcare template.

4. The method of claim 1, wherein generating an updated healthcare template comprises comparing a history associated with the user input to the criteria and adding a data option to the updated healthcare template when the history satisfies the criteria.

5. The method of claim 1, wherein generating an updated healthcare template comprises responding to the user input being a data option selection by displaying patient data corresponding to the data option selection on the updated healthcare template.

6. The method of claim 1, wherein the collaborative filtering is based on at least one variable selected from the group consisting of years of training, years of experience, physician status, specialty, board certifications, number of patients seen, number of patients admitted by the physician, and search term distribution over patients.

7. The method of claim 1, wherein:
    generating the first list comprises generating a first list sorted by one or both of popularity or feedback; and
    displaying the first list comprises displaying the sorted list.

8. The method of claim 1, further comprising:
    (1) receiving user input after displaying the second list of recommended information items, wherein the user input includes at least one of (1) a selection of an information item on the second list, or (2) a search term outside of the information items on the second list;
    (2) generating and displaying a fourth list of recommended information items in response to the user input representing the selection of an information item from the second list, wherein the fourth list of recommended information items is based on the selected information item from the second list, and collaborative filtering of the information in the one or more databases associated with the set of similar patients and the set of similar physicians; and
    (3) generating and displaying a fifth list of recommended information items in response to the user input representing the selection of the search term outside of the information items on the second list, wherein the fifth list of recommended information items is based on the search term outside of the information items on the second list, and collaborative filtering of the information in the one or more databases associated with the set of similar patients and the set of similar physicians; and
    (4) optionally repeating steps (1)-(3) one or more times in response to user input following the generation and display of one or both of the fourth list or fifth list of recommended information items.

9. The method of claim 1, further comprising:
    (1) receiving user input after displaying the third list of recommended information items, wherein the user input includes at least one of (1) a selection of an information item on the third list, or (2) a search term outside of the information items on the third list;
    (2) generating and displaying a fourth list of recommended information items in response to the user input representing the selection of an information item from the third list, wherein the fourth list of recommended information items is based on the selected information item from the third list, and collaborative filtering of the information in the one or more databases associated with the set of similar patients and the set of similar physicians; and
    (3) generating and displaying a fifth list of recommended information items in response to the user input representing the selection of the search term outside of the information items on the third list, wherein the fifth list of recommended information items is based on the search term outside of the information items on the third list, and collaborative filtering of the information in the one or more databases associated with the set of similar patients and the set of similar physicians; and (4) optionally repeating steps (1)-(3) one or more times in response to user input following the generation and display of one or both of the fourth list or fifth list of recommended information items.

10. A system for generating a health management template for a patient condition comprising:
a data interface in electrical communication with a processor, a patient database, a user interface, and a template database;
the user interface configured to retrieve a healthcare template corresponding to a patient condition, the healthcare template comprising a plurality of data fields, and wherein the user interface includes both a search request selection and a data option selection;
populating, by the user interface, the plurality data fields with patient data; and
generating, by the processor, an updated healthcare template based on a user input comprising a search request selection, comprising:
  identifying in the patient database a set of plurality of similar physicians having similarities to the user;
  identifying in the patient database a set of a plurality of similar patients having similarities to the patient;
  generating and displaying a first list of recommended information items based on collaborative filtering of information in the patient database associated with the set of similar physicians and the set of similar patients;
  receiving user input after displaying the first list of recommended information items, wherein the user input includes at least one of (1) a selection of an information item on the first list, or (2) a search term outside of the information items on the first list;
  generating and displaying a second list of recommended information items in response to the user input representing the selection of an information item from the first list, wherein the second list of recommended information items is based on the selected information item from the first list, and collaborative filtering of the information in the patient database associated with the set of similar patients and the set of similar physicians; and
  generating and displaying a third list of recommended information items in response to the user input representing the selection of the search term outside of the information items on the first list, wherein the third list of recommended information items is based on the search term outside of the information items on the first list, and collaborative filtering of the information in the patient database associated with the set of similar patients and the set of similar physicians; and
generating, by the processor, an updated healthcare template based on a user input comprising a data option selection, comprising:
  comparing a history associated the data option selection to a criteria, wherein the criteria comprises at least one of a popularity of the data option selection request or an importance of the data option selection; and
  adding a data field corresponding to the data option selection to the updated healthcare template when the history satisfies the criteria.

11. The system of claim 10, further comprising receiving data indicating the patient condition.

12. The system of claim 10, further comprising generating, by the processor, an updated healthcare template in response to additional data from the user by retrieving additional data fields and adding the additional data fields to the updated healthcare template.

13. The method of claim 10, wherein:
generating the first list comprises generating a first list sorted by one or both of popularity or feedback; and
displaying the first list comprises displaying the sorted list.

14. The method of claim 10, wherein generating by the processor further comprises:
(1) receiving user input after displaying the second list of recommended information items, wherein the user input includes at least one of (1) a selection of an information item on the second list, or (2) a search term outside of the information items on the second list;
(2) generating and displaying a fourth list of recommended information items in response to the user input representing the selection of an information item from the second list, wherein the fourth list of recommended information items is based on the selected information item from the second list, and collaborative filtering of the information in the patient database associated with the set of similar patients and the set of similar physicians; and
(3) generating and displaying a fifth list of recommended information items in response to the user input representing the selection of the search term outside of the information items on the second list, wherein the fifth list of recommended information items is based on the search term outside of the information items on the second list, and collaborative filtering of the information in the patient database associated with the set of similar patients and the set of similar physicians; and
(4) optionally repeating steps (1)-(3) one or more times in response to user input following the generation and display of one or both of the fourth list or fifth list of recommended information items.

15. The method of claim 10, wherein generating by the processor further comprises:
(1) receiving user input after displaying the third list of recommended information items, wherein the user input includes at least one of (1) a selection of an information item on the third list, or (2) a search term outside of the information items on the third list;
(2) generating and displaying a fourth list of recommended information items in response to the user input representing the selection of an information item from the third list, wherein the fourth list of recommended information items is based on the selected information item from the third list, and collaborative filtering of the information in the patient database associated with the set of similar patients and the set of similar physicians; and
(3) generating and displaying a fifth list of recommended information items in response to the user input representing the selection of the search term outside of the information items on the third list, wherein the fifth list of recommended information items is based on the search term outside of the information items on the third list, and collaborative filtering of the information in the patient database associated with the set of similar patients and the set of similar physicians; and (4) optionally repeating steps (1)-(3) one or more times in response to user input following the generation and display of one or both of the fourth list or fifth list of recommended information items.

16. A non-transitory computer readable storage medium bearing instructions for generating a health management template for a patient condition, the instructions, when executed by a processor in electrical communication with a template database, cause the processor to perform operations comprising:

retrieving a healthcare template from the template database corresponding to a patient condition, the healthcare template comprising a plurality of data fields;

populating the data fields with patient data; and generating a user interface to receive user input, wherein the user interface includes both a search request selection and a data option selection;

generating an updated healthcare template based on the user input comprising a search request selection, comprising:

identifying in one or more databases a set of plurality of similar physicians having similarities to a user;

identifying in the one or more databases a set of a plurality of similar patients having similarities to the patient;

generating and displaying a first list of recommended information items based on collaborative filtering of information in the one or more databases associated with the set of similar physicians and the set of similar patients;

receiving user input after displaying the first list of recommended information items, wherein the user input includes at least one of (1) a selection of an information item on the first list, or (2) a search term outside of the information items on the first list;

generating and displaying a second list of recommended information items in response to the user input representing the selection of an information item from the first list, wherein the second list of recommended information items is based on the selected information item from the first list, and collaborative filtering of the information in the one or more databases associated with the set of similar patients and the set of similar physicians; and generating and displaying a third list of recommended information items in response to the user input representing the selection of the search term outside of the information items on the first list, wherein the third list of recommended information items is based on the search term outside of the information items on the first list, and collaborative filtering of the information in the one or more databases associated with the set of similar patients and the set of similar physicians; and generating an updated healthcare template based on the user input comprising the data option selection, comprising comparing a history associated with the data option selection to a criteria, wherein the criteria comprises at least one of a popularity of the data option selection request or an importance of the data option selection; and adding a data field corresponding to the data option selection to the updated healthcare template when the history satisfies the criteria.

17. The non-transitory computer readable storage medium of claim 16, further comprising generating an updated healthcare template in response to additional data from the user by retrieving additional data fields and adding the additional data fields to the updated healthcare template.

\* \* \* \* \*